United States Patent
Sako et al.

(10) Patent No.: US 9,566,180 B2
(45) Date of Patent: Feb. 14, 2017

(54) STIMULUS GENERATION APPARATUS

(71) Applicant: SONY CORPORATION, Tokyo (JP)

(72) Inventors: Yoichiro Sako, Tokyo (JP); Maiko Saitou, Tokyo (JP); Takayuki Hirabayashi, Tokyo (JP); Hideki Sakai, Kanagawa (JP); Takatoshi Nakamura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 507 days.

(21) Appl. No.: 13/955,215

(22) Filed: Jul. 31, 2013

(65) Prior Publication Data

US 2014/0051905 A1 Feb. 20, 2014

(30) Foreign Application Priority Data

Aug. 16, 2012 (JP) ................. 2012-180314

(51) Int. Cl.
| | | |
|---|---|---|
| *A61N 2/00* | (2006.01) | |
| *A61F 5/00* | (2006.01) | |
| *A61N 1/05* | (2006.01) | |
| *A61F 7/12* | (2006.01) | |
| *A61M 5/172* | (2006.01) | |
| *A61F 7/10* | (2006.01) | |
| *A61B 1/04* | (2006.01) | |
| *A61N 1/20* | (2006.01) | |
| *A61N 1/372* | (2006.01) | |

(Continued)

(52) U.S. Cl.
CPC ........... *A61F 5/003* (2013.01); *A61B 1/00009* (2013.01); *A61B 1/041* (2013.01); *A61F 7/106* (2013.01); *A61F 7/12* (2013.01); *A61M 5/1723* (2013.01); *A61N 1/0509* (2013.01); *A61N 1/205* (2013.01); *A61N 1/37205* (2013.01); *A61F 7/034* (2013.01); *A61F 2007/0075* (2013.01); *A61F 2007/029* (2013.01); *A61N 2/006* (2013.01)

(58) Field of Classification Search
CPC ............ A61F 5/003; A61F 7/106; A61F 7/12; A61F 7/034; A61F 2007/029; A61F 2007/0075; A61B 1/00009; A61B 1/041; A61B 1/042; A61N 1/37205; A61N 1/205; A61N 1/0509; A61N 2/006; A61M 5/1723
See application file for complete search history.

(56) References Cited

U.S. PATENT DOCUMENTS

| | | | | |
|---|---|---|---|---|
| 2005/0183733 | A1* | 8/2005 | Kawano | A61B 1/00156 128/899 |
| 2008/0086179 | A1* | 4/2008 | Sharma | A61N 1/36007 607/40 |

(Continued)

FOREIGN PATENT DOCUMENTS

| | | |
|---|---|---|
| JP | 2005-204806 A | 8/2005 |
| JP | 2007-014634 A | 1/2007 |

OTHER PUBLICATIONS

Bjørndal, B., Burri, L., Staalesen, V., Skorve, J., & Berge, R. K. (2011). Different Adipose Depots: Their Role in the Development of Metabolic Syndrome and Mitochondrial Response to Hypolipidemic Agents. Journal of Obesity, 2011, 490650. http://doi.org/10.1155/2011/490650.*

*Primary Examiner* — John Lacyk
(74) *Attorney, Agent, or Firm* — Chip Law Group

(57) ABSTRACT

There is provided a stimulus generation apparatus including a stimulus generation section which provides a stimulus for promoting fat burning for fat or a satiety center inside a body cavity.

10 Claims, 10 Drawing Sheets

(51) Int. Cl.
  *A61B 1/00* (2006.01)
  *A61F 7/03* (2006.01)
  *A61F 7/00* (2006.01)
  *A61F 7/02* (2006.01)

(56) References Cited

U.S. PATENT DOCUMENTS

2011/0034769 A1* 2/2011 Adair ................. A61B 1/00016
  600/110
2011/0270360 A1* 11/2011 Harris ...................... A61N 1/36
  607/62

* cited by examiner

STIMULUS GENERATION APPARATUS

BACKGROUND

The present disclosure relates to a stimulus generation apparatus.

Nowadays, a capsule type medical apparatus introduced into the body of a test subject is known. Randomly imaging each part within the body, gathering samples or the like from within the body, or progressively observing a prescribed part by remaining inside the body cavity such as disclosed in JP 2007-14634A and JP 2005-204806A, are known as such a capsule type medical apparatus.

SUMMARY

However, none of these propose generating a stimulus for promoting fat burning inside the body cavity.

Accordingly, the present disclosure proposes a stimulus generation apparatus capable of promoting fat burning.

According to the present disclosure, a stimulus generation apparatus is proposed including a stimulus generation section which provides a stimulus for promoting the burning of fat, in fats or in the satiety center, inside the body cavity.

According to the present disclosure as described above, it becomes possible to promote fat burning.

DETAILED DESCRIPTION OF THE EMBODIMENT(S)

Figure 1:
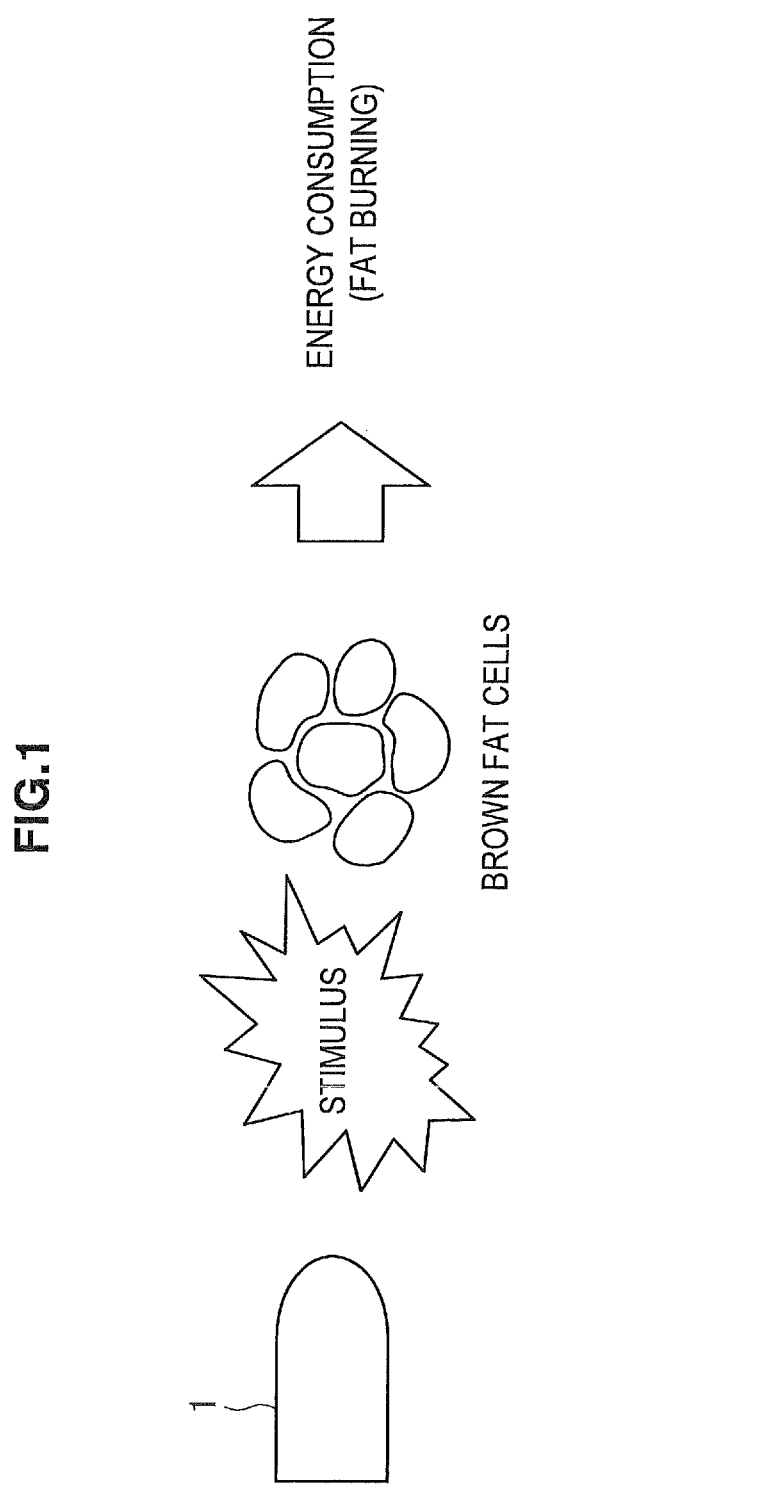
FIG. 1 is a figure for describing an outline of a fat burning system according to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.

1. The First Embodiment
1-1. Outline
1-2. Configuration of the capsule
1-3. Operation processes
1-4. Modified examples
2. The Second Embodiment
2-1. Outline
2-2 Configuration of the capsule
3. Conclusion <1. The First Embodiment>
[1-1. Outline]

First, an outline of a fat burning system according to a first embodiment of the present disclosure will be described with reference to FIG. 1. As shown in FIG. 1, in the fat burning system according to the present embodiment, a capsule type medical apparatus 1 (stimulus generation apparatus) introduced into the body cavity of a test subject can promote fat burning by providing a stimulus for ranges which include prescribed fats within the body cavity. Further, the capsule type medical apparatus 1 (hereinafter, called the capsule 1) according to the present embodiment can be introduced into a blood vessel or into the digestive organs.

(Background)

Here, there are 60 trillion cells in the human body, and one type from among these cells is fat cells, which perform synthesis, decomposition, and accumulation of fat. Further, the two types of "white fat cells" and "brown fat cells" are known in the fat cells. "White fat cells" have characteristics which accumulate large amounts of fat energy within the body as neutral fats, and are a cause of obesity. On the other hand, "brown fat cells" are different from white fat cells, and have characteristics which burn excess neutral fats accumulated within the body to be released as energy.

Therefore, the more the brown fat cells are active, the more the body fat will be consumed. To continue, the general process up to when the brown fat cells are active will be simply described.

First, when additional energy becomes neutral fat and is accumulated in white fat cells, a hormone called leptin is secreted from the fat tissue. Leptin acts on the brain via a leptin receptor which is located in the hypothalamus of the brain, suppresses the feeding center, and stimulates the satiety center. In this way, a person refrains from eating by a feeling of fullness. Further, the brain, which has received the signals of leptin, transmits signals to the sympathetic nerves so as to consume the additional energy. By this reception, actions of the brown fat cells are activated, and the neutral fats are burned and released as energy.

There are large individual variations in such actions of the brown fat cells, and while a person in which the actions of the brown fat cells is lively will have a predisposition towards fat being converted into energy, even if eating a little extra, and not easily becoming fat, a person in which the actions of the brown fat cells is bad will have a predisposition towards additional energy remaining in the body as body fat, the body easily becoming cold, and easily becoming fat.

However, even if there are strong individual variations in the actions of the brown fat cells, it is possible for the brown fat cells to be activated by providing a stimulus by cooling the brown fat cells. While generally methods such as "going swimming" or "taking a cold shower" have been proposed as methods which cool the brown fat cells, it may be necessary to go to a swimming pool or to go and take a shower, and neither one of these can be immediately and conveniently performed.

Further, since it may be possible to have a feeling of "cold" in the brain, activation of the brown fat cells can be prompted, even by providing a stimulus using ice, an refrigerant, or the like, in the palm of the hand or the like, for example, where tissue called "corpuscles" is densely formed, which have the role of temperature sensors in a person's body. However, it is time consuming and troublesome to prepare ice, an insulating material or the like. Further, a stimulus from the outside of the skin is also considered to be insufficient.

Accordingly, the point of view of this situation led to creating the fat burning system according to the first embodiment. The fat burning system according to the first embodiment activates the brown fat cells and promotes fat burning, by providing a stimulus for ranges which include the brown fat cells inside the body cavity.

Heretofore, an outline of the present embodiment has been described. To continue, a configuration of the capsule 1 and the operation processes according to the present embodiment will be sequentially described.

[1-2. Configuration of the Capsule]

Figure 2:
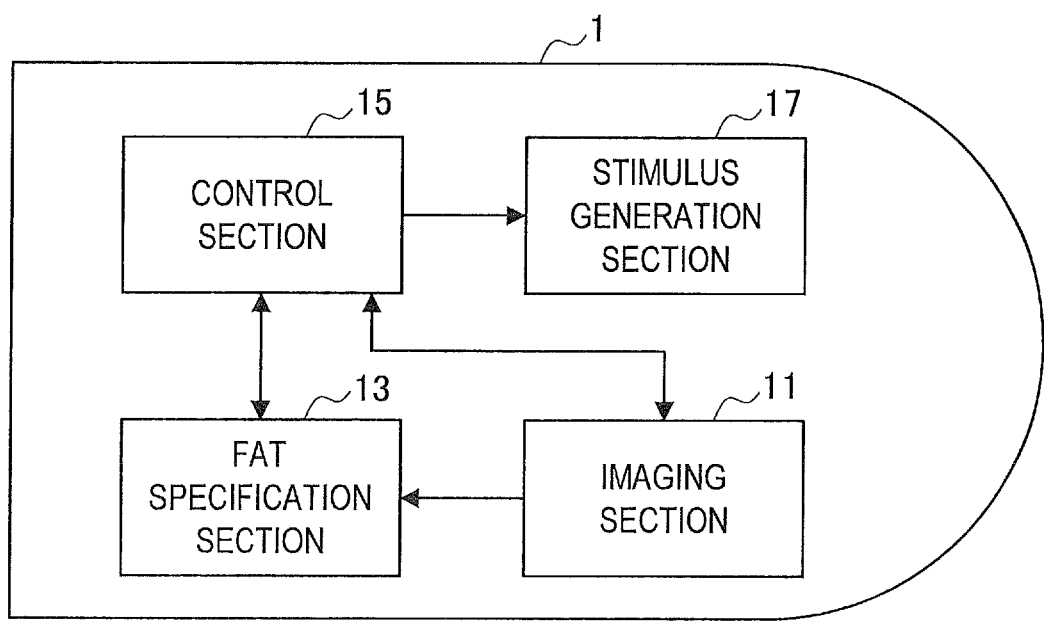
FIG. 2 is a block diagram which shows a configuration of a capsule according to the first embodiment.

FIG. 2 is a block diagram which shows a configuration of the capsule 1 according to the first embodiment. As shown in FIG. 2, the capsule 1 has an imaging section 11, a fat specification section 13, a control section 15, and a stimulus generation section 17.

(Imaging Section)

The imaging section 11 is implemented by an illumination section such as a white LED (Light Emitting Diode), an imaging optical system which includes an imaging lens, and an imaging element (CMOS imager, CCD or the like). In this way, the capsule 1 irradiates inside the body cavity by the white LED or the like while moving inside the body cavity, and can image inside the body cavity.

(Control Section)

The control section 15 controls each constituent element of the capsule 1. Specifically, the control section 15 may function as a judgment section which judges whether or not the capsule 1 has reached a prescribed part, based on picked-up images of inside the body cavity imaged by the imaging section 11. For example, the control section 15 (judgment section) judges whether or not the capsule 1 has reached a prescribed part registered in advance as a stimulus position. In the case where it is judged that the capsule 1 has reached the prescribed part, the control section 15 controls the fat specification section 13 so as to specify prescribed fats (of the position), based on the picked-up images.

Further, when the prescribed fats or the surroundings of the prescribed fats are specified by the fat specification section 13, the control section 15 controls the stimulus generation section 17 so as to provide a stimulus for the specified fats or surroundings of the fats.

(Fat Specification Section)

The fat specification section 13 analyzes the picked-up images, and specifies the prescribed fats or the surroundings of the prescribed fats. For example, the fat specification section 13 specifies brown fat cells by analyzing the colors of the picked-up images. Further, other than brown fat cells, the fat specification section 13 may specify neutral fats or vascular fats.

(Stimulus Generation Section)

The stimulus generation section 17 provides a stimulus for ranges which include the prescribed fats of inside the body cavity. Here, the stimulus generation section 17 can generate at least a mechanical, electrical, magnetic or chemical stimulus. Further, the stimulus provided by the stimulus generation section 17 may be a vibrational stimulus, a pressure stimulus, an electrical stimulus, a magnetic stimulus, a heating stimulus, or a cooling stimulus. For example, a vibrational stimulus can be provided by implementing the stimulus generation section 17 by a vibration motor which is constituted by a coreless motor and an eccentric weight. Further, an electrical stimulus can be provided by implementing the stimulus generation section 17 by a plurality of electrodes, and applying a current to the prescribed fats from the plurality of electrodes. Further, a pressure stimulus can be provided by implementing the stimulus generation section 17 by a solenoid, which is driven so as to push-expand a pantograph structure, or an actuator such as a DC motor, which is driven so as to push-expand a jack, and mechanically transforming the capsule 1.

Further, a heating stimulus or a cooling stimulus can be provided by implementing the stimulus generation section 17 by a cold temperature section, and generating heat (heating) or cold (cooling) so as to change the temperature of the prescribed fats. More specifically, heat generation control may be implemented by using an electrothermal coil (nichrome wire or the like), a peltier element, or an exothermic reaction (oxidation of metal or organic matter, hydration of quicklime or the like). Further, cold control may be implemented by using, for example, a peltier element or an endothermic reaction (dissolution of ammonium nitrate into water or the like).

[1-3. Operation Processes]

Heretofore, a configuration of the capsule 1 according to the present embodiment has been described in detail. To continue, the operation processes of the capsule 1 according to the present embodiment will be described with reference to FIG. 3.

Figure 3:
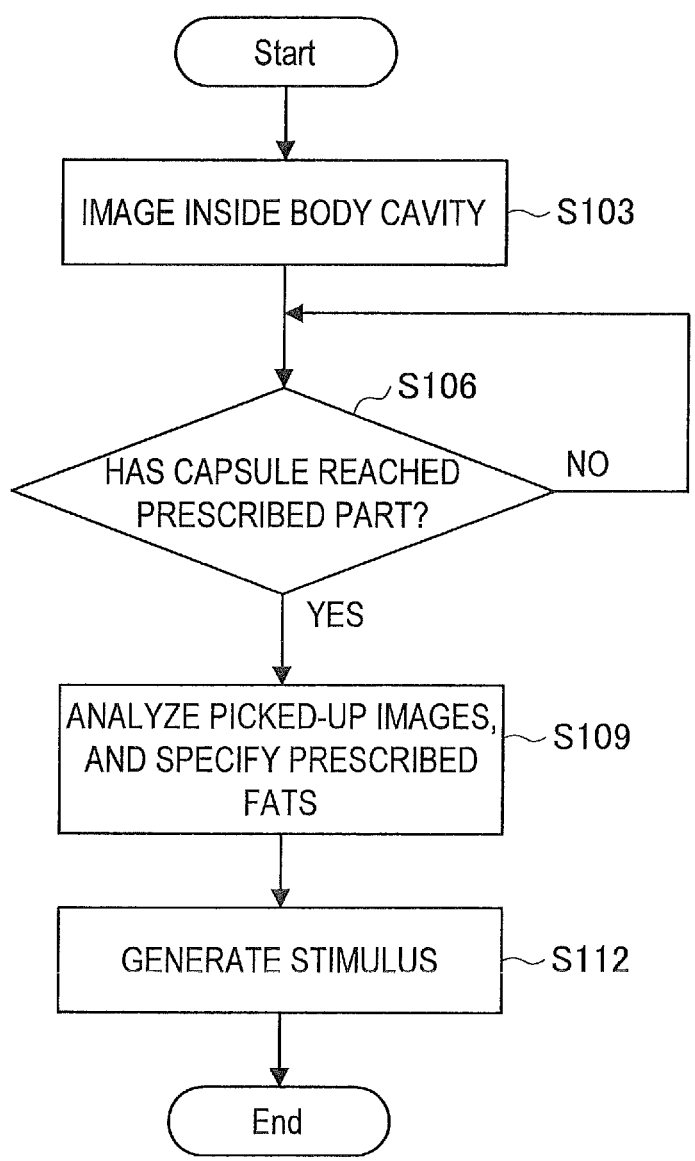
FIG. 3 is a flow chart which shows the operation processes of the capsule according to the first embodiment.

FIG. 3 is a flow chart which shows the operation processes of the capsule 1 according to the first embodiment. As shown in FIG. 3, first in step S103, the imaging section 11 of the capsule 1, which moves inside the body cavity, images inside the body cavity.

Next, in step S106, the control section 15 judges whether or not the capsule 1 has reached a prescribed part, based on the picked-up images of inside the body cavity imaged by the imaging section 11.

Next, in the case where it is judged that the capsule 1 has reached the prescribed part, in step S109, the fat specification section 13 analyzes the picked-up images, and specifies the prescribed fats. For example, the fat specification section 13 analyzes the colors of the picked-up images, and specifies brown fat cells.

Next, in step S112, the control section 15 controls the stimulus generation section 17 so as to provide a stimulus for ranges which include the fats specified by the fat specification section 13. For example, the control section 15 controls the stimulus generation section 17 so as to cool ranges which include brown fat cells. In this way, the brown fat cells are activated, and fat burning is promoted.

Heretofore, the operation processes of the capsule 1 according to the first embodiment of the present disclosure have been described in detail. Next, modified examples of the present embodiment will be described.

[1-4. Modified Examples]

(1-4-1. First Modified Example)

While a capsule type medical apparatus introduced inside the body cavity of a test subject is used as an example of a stimulus generation apparatus in the above described embodiment, the form of the stimulus generation apparatus according to the present embodiment is not limited to that of a capsule type.

Figure 4:
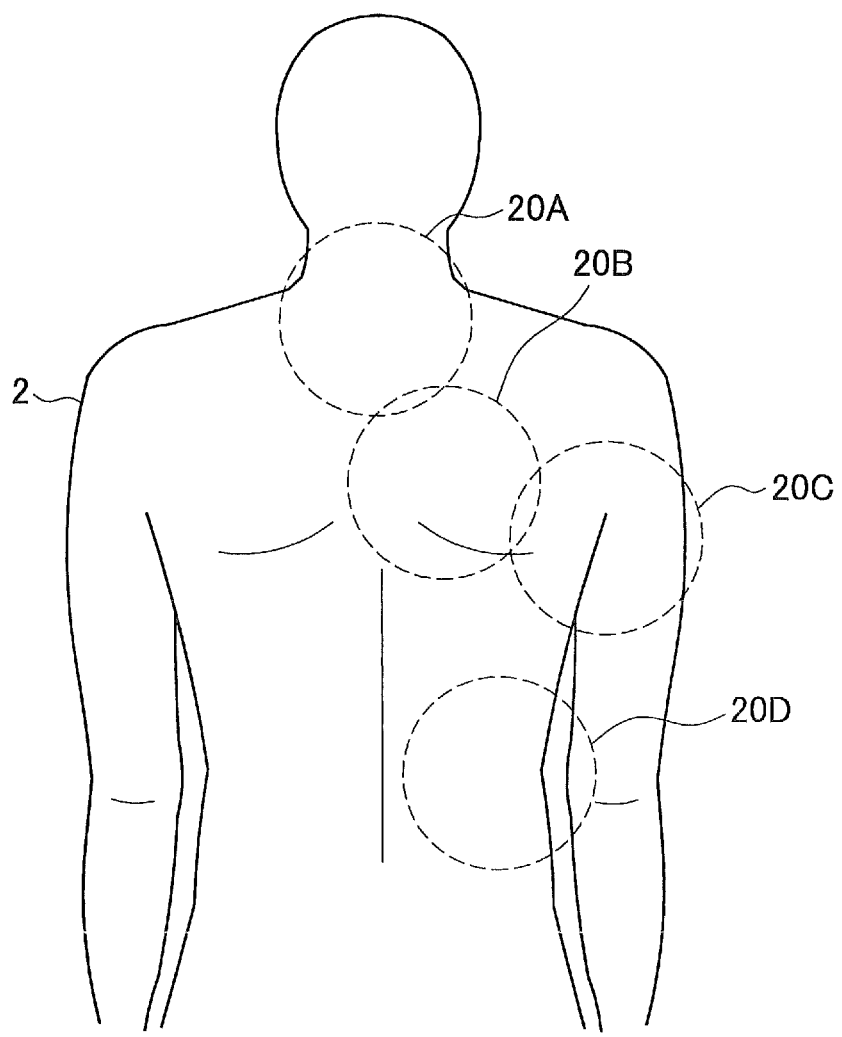
FIG. 4 is a figure for describing the parts at which brown fat cells gather.

Here, brown fat cells generally gather in parts 20A to 20D such as shown in FIG. 4. Specifically, the surroundings of the neck (part 20A), around the scapula (part 20B), under the armpits (part 20C), and the surroundings of the kidneys (part 20D). Therefore, fat burning can be further promoted by cooling such dense parts of brown fat cells inside the body cavity.

Accordingly, the brown fat cells which gather in parts such as those described above can be cooled within the body, by making the stimulus generation apparatus according to the present embodiment that of an endoscope type. Hereinafter, this will be specifically described with reference to FIG. 5.

Figure 5:
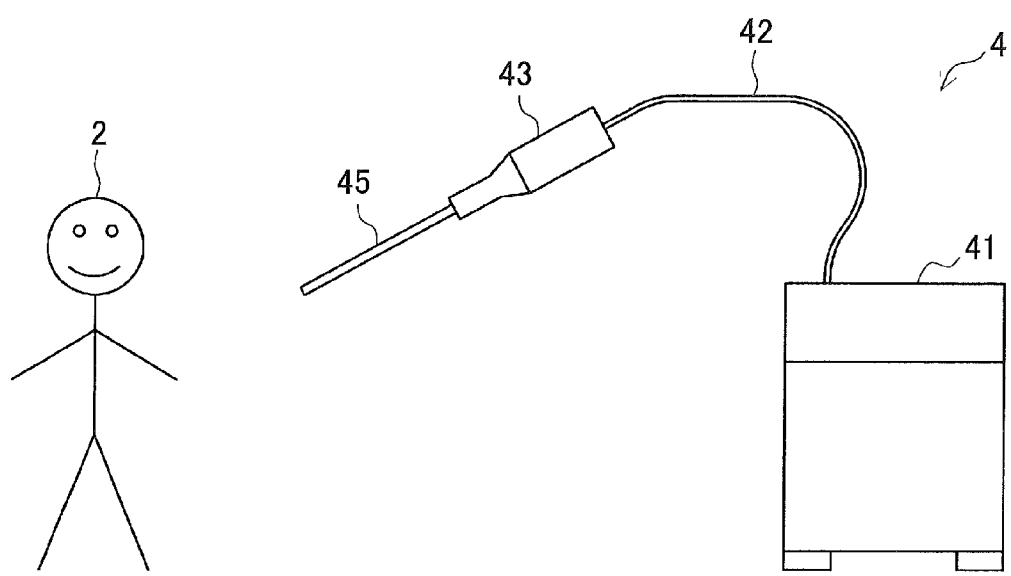
FIG. 5 is a figure for describing an endoscope type medical apparatus according to a first modified example.

FIG. 5 is a figure for describing an endoscope type medical apparatus 4 according to a first modified example. As shown in FIG. 5, the endoscope type medical apparatus 4 (hereinafter, called the endoscope 4) has a body section 41, a cable 42, a grasping section 43, and an insertion section 45.

The body section 41 has the functions of the fat specification section 13 and the control section 15 shown in FIG. 2. Further, the cable 42 is connected to the body section 41, and the cable 42 is connected to the grasping section 43.

The insertion section 45, which is inserted into the body from a skin incision of a test subject 2, is included in the grasping section 43. The functions of the imaging section 11 and the stimulus generation section 17 shown in FIG. 2 are included in a terminal of the insertion section 45 according to the present embodiment.

In this way, the endoscope 4 according to the present modified example inserts the insertion section 45 from a skin incision into a part at which brown fat cells are gathered, for example, such as the parts described with reference to FIG. 4, provides a cooling stimulus inside the body cavity upon specifying the brown fat cells, and can better activate the brown fat cells.

(1-4-2. Second Modified Example)

Further, while the fat burning system according to the above described embodiment performs a process in which a capsule 1 provides a stimulus to prescribed fats within the body of a test subject independently, the stimulus generation apparatus according to the present embodiment is not limited to that of such an independent type. For example, the fat burning system according to the present embodiment has a capsule type medical apparatus and a control apparatus, and this capsule type medical apparatus may be a dependent type which operates in accordance with control signals transmitted from the control apparatus. Hereinafter, this will be specifically described with reference to FIGS. 7 and 8.

(Configuration)

Figure 6:
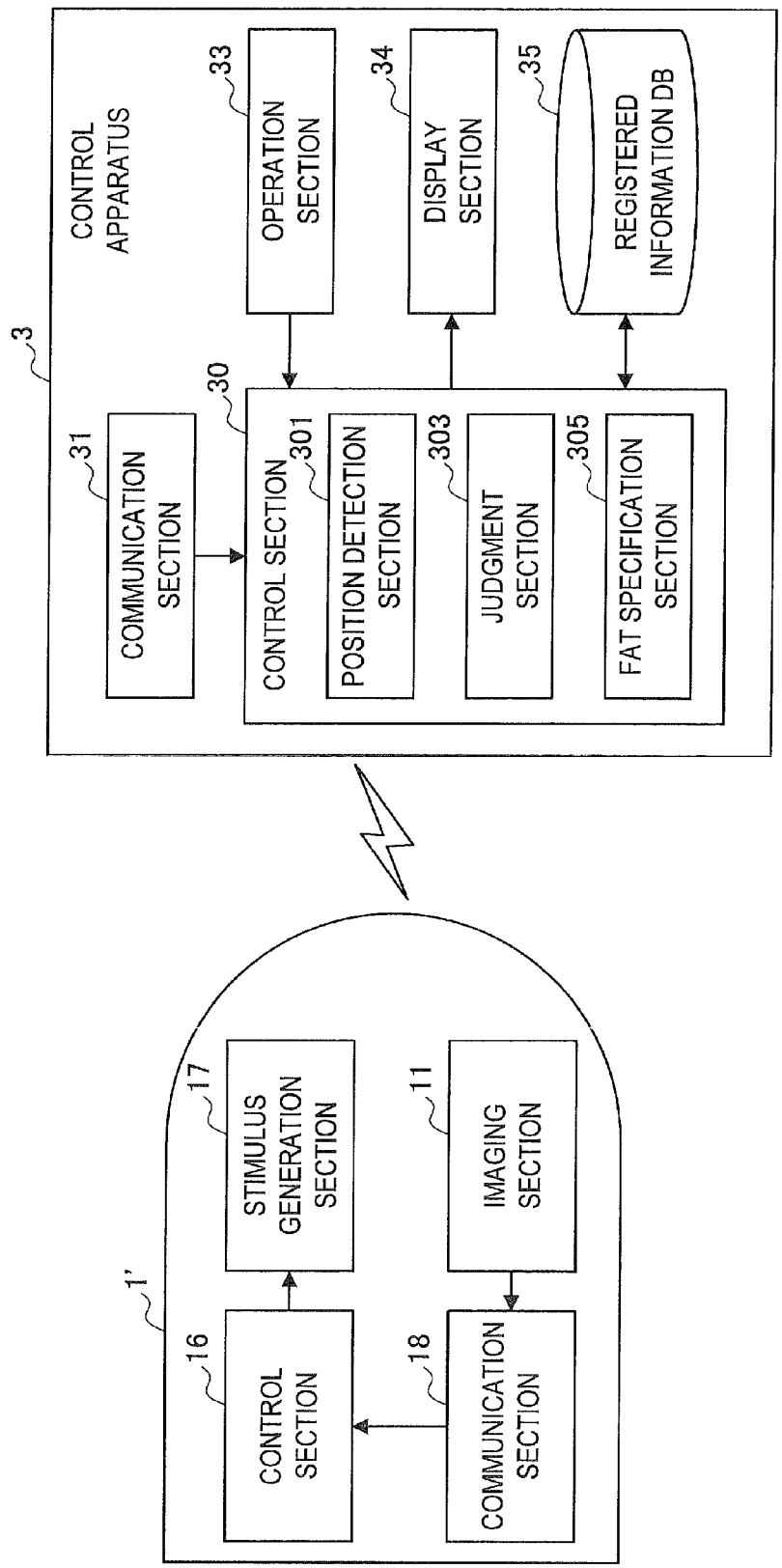
FIG. 6 is a block diagram which shows a configuration of a capsule type medical apparatus and a control apparatus included in a fat burning system according to a second modified example.

FIG. 6 is a block diagram which shows a configuration of a capsule type medical apparatus 1' and a control apparatus 3 included in the fat burning system according to a second modified example.

*Capsule Type Medical Apparatus

As shown in FIG. 6, the capsule type medical apparatus 1' (hereinafter, called the capsule 1') has an imaging section 11, a communication section 18, a control section 16, and a stimulus generation section 17. Since the imaging section 11 and the stimulus generation section 17 have been described above with reference to FIG. 2, a description of them will be omitted here.

The communication section 18 is a communication module which performs transmission/reception of data with an external apparatus. Specifically, the communication section 18 according to the present embodiment transmits signals for position detection, and the picked-up images of inside the body cavity imaged by the imaging section 11, to the control apparatus 3, and receives control signals from the control apparatus 3.

The control section 16 controls each constituent element of the capsule 1', in accordance with the control signals received by the communication section 18 from the control apparatus 3. For example, in the case where control signals (stimulus generation instructions) are received which instruct so as to provide a stimulus to ranges which include the prescribed fats, the control section 16 generates a stimulus by controlling the stimulus generation section 17.

*Control Apparatus

As shown in FIG. 6, the control apparatus 3 has a control section 30, a communication section 31, an operation section 33, a display section 34, and a registered information DB (Database) 35.

The communication section 31 is connected to an external apparatus, and has a function which performs transmission/reception of data. For example, the communication section 31 according to the present embodiment receives signals for position detection from the capsule 1', and transmits control signals to the capsule 1'.

The operation section 33 accepts operations by a user such as a medical staff or a test subject 2, and has a function which outputs input signals corresponding to the operation inputs to the control section 30. Further, the operation section 33 may be implemented by a mouse, keyboard, touch panel or the like.

The display section 34 has a function which performs a screen display including images and text, in accordance with the controls of the control section 30. Specifically, the display section 34 according to the present embodiment may display an operation screen related to the control of the capsule 1', or a stimulus setting screen which performs various settings related to a stimulus provided by the capsule 1'. Note that the display section 34 may be implemented by an LCD (Liquid Crystal Display), an OLED (Organic Light-Emitting Diode), a CRT (Cathode Ray Tube) or the like.

Figure 7:
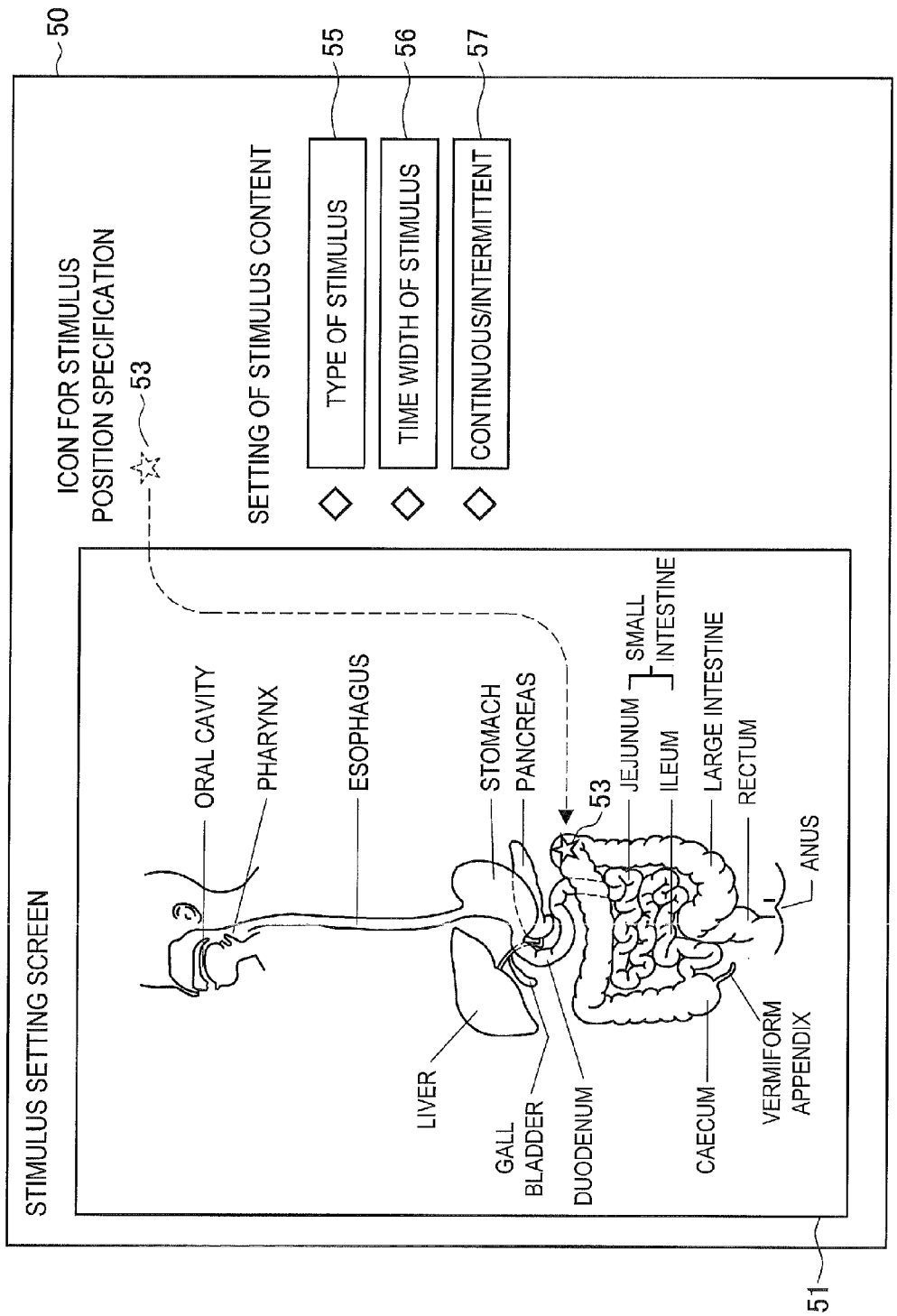
FIG. 7 is a figure which shows an example of a stimulus setting screen according to the present embodiment.

Here, an example of a stimulus setting screen displayed by the display section 34 according to the present embodiment is described with reference to FIG. 7. FIG. 7 is a figure which shows an example of a stimulus setting screen according to the present embodiment.

As shown in FIG. 7, the stimulus setting screen 50 includes a parts screen 51 which shows each part within the body, an icon 53 for stimulus position specification, and setting buttons 55 to 57 which perform various settings of the stimulus content.

In the parts screen 51, illustrations and names of each part of the digestive organs, in which the capsule 1' is introduced, are associated with each other. A user selects then icon 53 by operating the operation section 33, moves the icon 53 to a desired specific part (for example, a part at which it is assumed that brown fat cells or neutral fats are gathered) by a drag and drop operation, as shown in FIG. 7, and registers a stimulus position.

Next, the user selects the setting buttons 55 to 57, and performs various settings of the stimulus content. Specifically, for example, in the case where the type of stimulus is set, the user selects the setting button 55. With the setting button 55, for example, a mechanical stimulus, an electrical stimulus, a magnetic stimulus, a chemical stimulus, a heating/cooling stimulus or the like can be registered as the type of stimulus.

Further, in the case where the time width of the stimulus is set, the user selects the setting button 56. With the setting button 56, an arbitrary number of seconds or minutes can be registered as the time width of the stimulus.

Further, in the case where the timing of the stimulus is set, the user selects the setting button 57. The setting button 57 can register whether a continuous stimulus is generated, or whether an intermittent stimulus is generated, as the timing of the stimulus.

Heretofore, while a screen for performing a variety of stimulus settings has been described with reference to FIG. 7 in the case where the capsule 1' is introduced into the digestive organs, the stimulus setting screen according to the present embodiment is not limited to this, and may be a screen for performing various stimulus settings, for example, in the case where the capsule 1' is introduced into a blood vessel.

Further, various information related to stimulus generation registered by the above described stimulus setting screen 50 is kept in the registered information DB 35.

The control section 30 has a function which controls each constituent element of the control apparatus 3. Specifically, as shown in FIG. 6, the control section 30 according to the present embodiment functions as a position detection section 301, a judgment section 303, and a fat specification section 305.

The position detection section 301 detects (calculates) the position of the capsule 1', based on the signals for position detection received by the communication section 31 from the capsule 1'. Also, the position detection section 301 outputs position information of the detected capsule 1' to the judgment section 303. Note that the position detection section 301 may detect the position of the capsule 1' based on a field intensity when an antenna (not shown in the figures) included in a shield shirt worn by the test subject receives the signals for position detection from the capsule 1' within the body.

Further, other than the signals for position detection, the position detection section 301 may detect the position of the capsule 1' by analyzing the picked-up images received from the capsule 1', or may detect the position of the capsule 1' based on values (pH values or the like) detected by various sensors (not shown in the figures) of the capsule 1'.

The judgment section 303 judges whether or not the position of the capsule 1' detected by the position detection section 301 is in the vicinity of a prescribed part (stimulus location) registered in advance by a medical staff, a test subject or the like. Note that the judgment section 303 extracts information related to the prescribed part from the registered information DB 35.

Since the fat specification section 305 has a function similar to that of the fat specification section 13 described above with reference to FIG. 2, a description of it will be omitted here.

Heretofore, each constituent element of the capsule 1' and the control apparatus 3 according to the present modified example has been described in detail. To continue, the operation processes of the fat burning system according to the present modified example will be described with reference to FIG. 8.

(Operation Processes)

Figure 8:
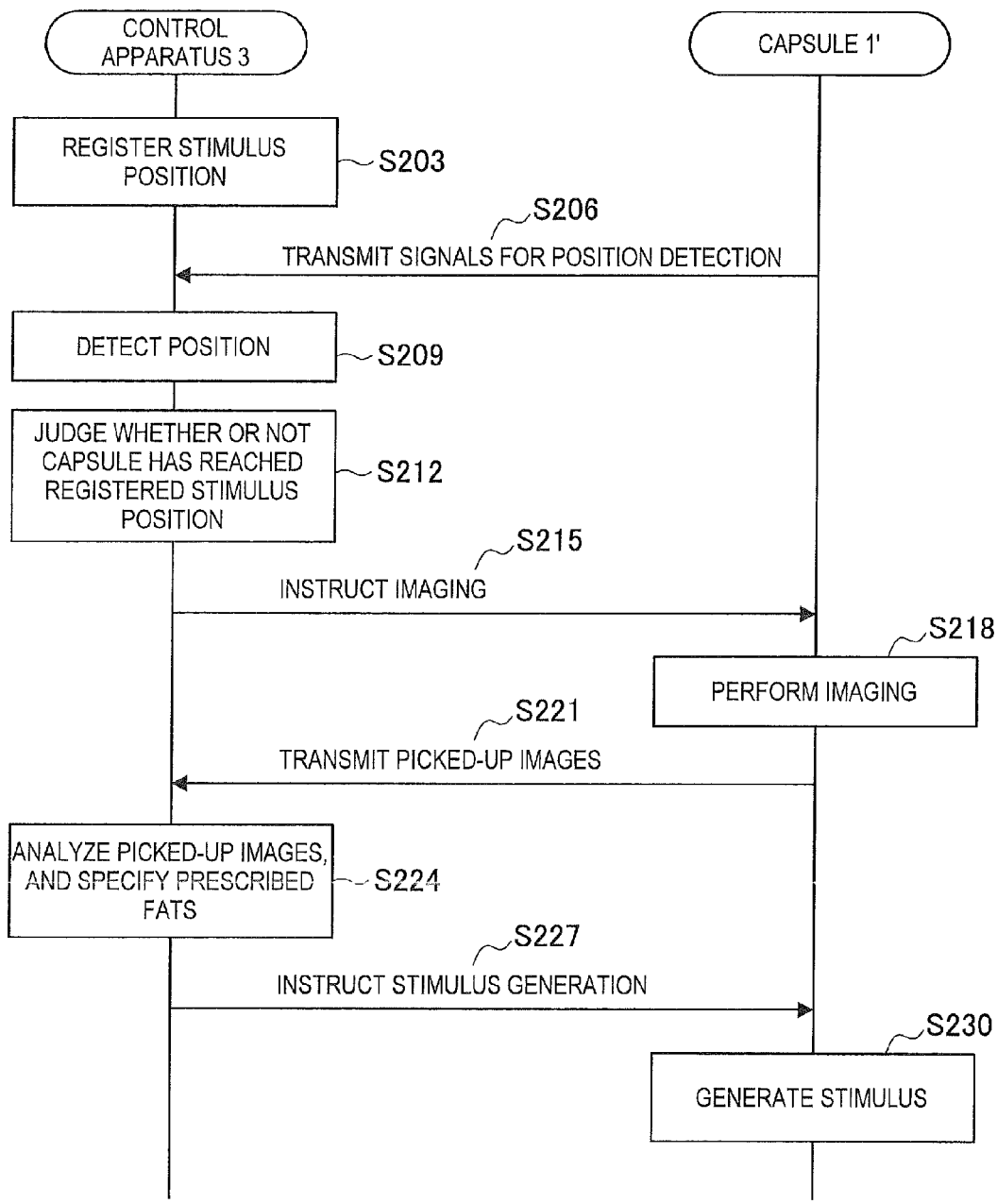
FIG. 8 is a flow chart which shows the operation processes of the fat burning system according to the second modified example.

FIG. 8 is a flow chart which shows the operation processes of the fat burning system according to the second modified embodiment. As shown in FIG. 8, first in step S203, the control apparatus 3 registers a stimulus position (prescribed part) in accordance with a user operation. Note that, apart from the stimulus position, the control apparatus 3 also registers various settings related to the stimulus in accordance with the user operation.

Next, in step S206, the capsule 1', which is introduced into the body cavity of the test subject by applying power, transmits signals for position detection to the control apparatus 3 while moving inside the body cavity.

Next, in step S209, the position detection section 301 of the control apparatus 3 detects the position of the capsule 1' based on the signals for position detection transmitted from the capsule 1'. Note that, as described above, the position detection section 301 may detect the position of the capsule 1' by analyzing the picked-up images of inside the body cavity transmitted from the capsule 1'.

To continue, in step S212, the judgment section 303 of the control apparatus 3 judges whether or not the position of the capsule 1' detected by the position detection section 301 is the stimulus position registered in the above described step S203. For example, in the case where the capsule 1' is positioned in the vicinity (within a prescribed range) of the stimulus position registered in advance, the judgment section 303 may judge that the capsule 1' has reached the stimulus position.

Next, in the case where it is judged by the judgment section 303 that the position of the capsule 1' has reached the stimulus position, in step S215, the control apparatus 3 controls the communication section 31, and transmits control signals, which instruct imaging, to the capsule 1'.

Next, in step S218, the control section 16 of the capsule 1' images inside the body cavity by the imaging section 11, in accordance with the control signals received via the communication section 18.

Next, in step S221, the communication section 18 of the capsule 1' transmits the picked-up images of inside the body cavity imaged by the imaging section 11 to the control apparatus 3.

Next, in step S224, the fat specification section 305 of the control apparatus 3 analyzes the picked-up images of inside the body cavity received by the communication section 31 from the capsule 1', and specifies prescribed fats. Here, the prescribed fats may be fats selected by a user in advance (for example, brown fat cells) on the stimulus setting screen 50.

Next, in step S227, the control apparatus 3 transmits the control signals, which instruct stimulus generation, from the communication section 31 to the capsule 1' so as to provide a stimulus for ranges which include the fats specified by the fat specification section 305. Here, information of various settings related to a stimulus registered in advance by a user may also be included in the control signals, which instruct stimulus generation, transmitted by the control apparatus 3.

Next, in step S230, the control section 16 of the capsule 1' controls the stimulus generation section 17, in accordance with the control signals received via the communication section 18, and provides a stimulus for ranges which include the specified stimulus. Further, the control section 16 controls the type of stimulus and the time width and timing of the stimulus, in accordance with the various settings related to the stimulus included in the control signals.

As described above, according to the fat burning system according to the second modified embodiment, the capsule 1' operates in accordance with control signals transmitted from the control apparatus 3, and can provide a stimulus for ranges which include prescribed fats.

Note that, in the example shown in FIG. 6, while the case where the capsule 1' and the control apparatus 3 are connected by wireless communication is described, the communication according to the present embodiment is not limited to that of wireless, and it may be wired. In this case, for example, the capsule 1' is introduced into the body cavity of a test subject in a state in which a communication line connected with the control apparatus 3 is attached, and the control apparatus 3 performs data communication with the capsule 1' via this communication line. Further, in the case where the capsule 1' and the control apparatus 3 are connected by wireless communication, the control apparatus 3 may be placed on the test subject, with an antenna (not shown in the figures) included in a shield shirt worn by the test subject, and may perform data communication with the capsule 1' via a communication apparatus connected with this antenna.

<2. The Second Embodiment>

The fat burning system according to the above described first embodiment is activated by providing a stimulus (for example, cooling) to brown fat cells having actions to convert, in particular, neutral fats into energy by burning the neutral fats, and promotes fat burning. However, the fat burning system according to the embodiments of the present disclosure is not limited to this, and they may promote fat burning, for example, by stimulating the satiety center.

(Background)

As described above, the feeding center is suppressed and the satiety center is stimulated by accepting leptin, which is secreted from fat tissue in the case where additional energy becomes neutral fat and is accumulated in white fat cells, by a leptin receptor of the brain. In this way, the brain transmits signals to the sympathetic nerves so as to consume the additional energy, and the actions of brown fat cells are also activated. However, when leptin is secreted in large amounts by fats increasing too much, a problem of leptin resistance occurs in which reaction by the leptin receptor is made difficult. When leptin resistance occurs, the brain is not able to accept leptin, and suppression of the feeding center and stimulus of the satiety center are not performed, even if additional energy is accumulated in the white fat cells. In this way, a feeling of fullness is not able to be obtained even if a lot of food is eaten, and will become a state in which fat burning is not promoted.

For such a problem, generally the secretion amount of leptin is inhibited by decreasing the amount of food consumed, and it is recommended to wait for the recovery of the leptin receptor by not imposing any load on the leptin receptor. However, in this case, since the secretion amount of leptin can be inhibited, suppression of the feeding center and stimulus of the satiety center will almost disappear, and since a feeling of fullness is not is not able to be felt, waiting for the recovery of the leptin receptor will not be easy.

Accordingly, a second embodiment according to the present disclosure proposes to make a sense of fullness be felt, by providing a stimulus to the satiety center with another method, even during the time when waiting for the recovery of the leptin receptor. Since the brain transmits signals to the sympathetic nerves so as to consume additional energy, if it is possible to provide a stimulus to the satiety center, fat burning will be promoted as a result. For example, serotonin and histamine are secreted in the brain, for example, by chewing well during a meal, and the satiety center will be stimulated even if leptin resistance occurs. Further, providing a stimulus to the satiety center can be considered by stimulating the stomach. Hereinafter, the fat burning system according to the present embodiment will be specifically described with reference to FIGS. 9 and 10.

[2-1. Outline]

Figure 9:
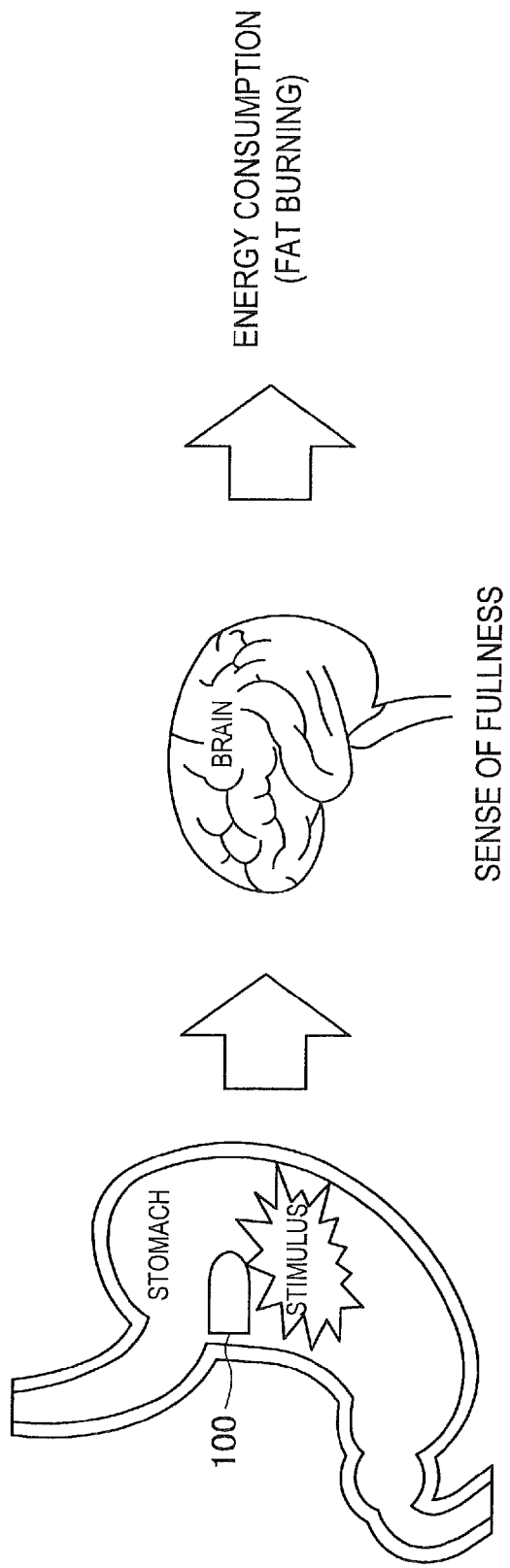
FIG. 9 is a figure for describing an outline of a fat burning system according to a second embodiment of the present disclosure.

FIG. 9 is a figure for describing an outline of the fat burning system according to the second embodiment. As shown in FIG. 9, a capsule type medical apparatus 100 (stimulus generation apparatus) according to the present embodiment suppresses the feeding center of the brain and stimulates the satiety center by generating, for example, a stimulus in the stomach. In this way, the brain feels a sense of fullness, transmits signals to the sympathetic nerves so as to consume additional energy, and fat burning is promoted.

[2-2. Configuration of the Capsule]

Figure 10:
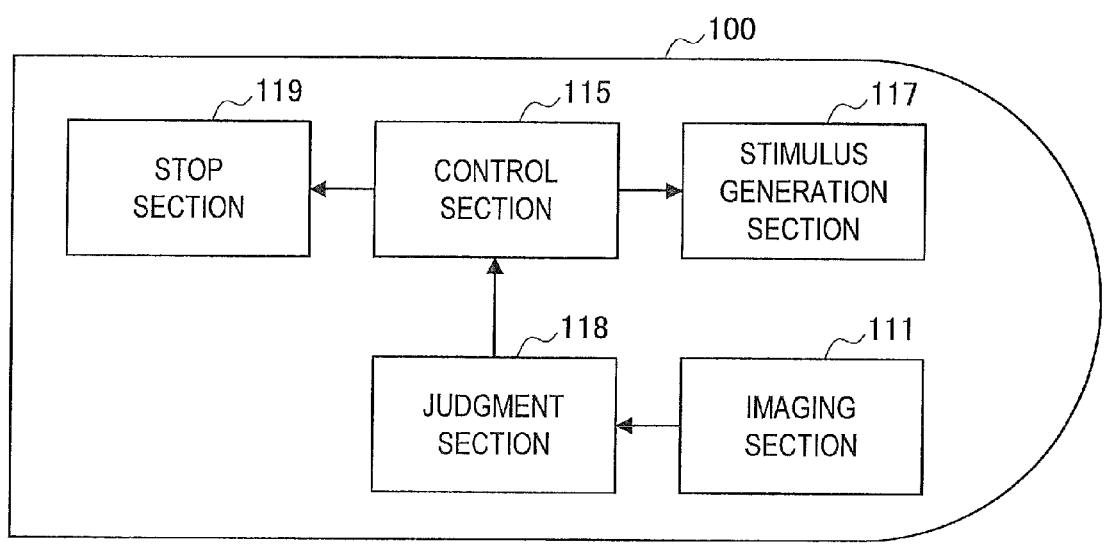
FIG. 10 is a block diagram which shows a configuration of a capsule type medical apparatus according to the second embodiment.

FIG. 10 is a block diagram which shows a configuration of the capsule type medical apparatus 100 according to the second embodiment. As shown in FIG. 10, the capsule type medical apparatus 100 (hereinafter, called the capsule 100) has an imaging section 111, a judgment section 118, a control section 115, a stimulus generation section 117, and a stop section 119.

(Imaging Section)

The imaging section 111 is implemented by an illumination section such as a white LED (Light Emitting Diode), an imaging optical system which includes an imaging lens, and an imaging element (CMOS imager, CCD or the like). In this way, the capsule 100 irradiates inside the body cavity by the white LED or the like while moving inside the body cavity, and can image inside the body cavity.

(Judgment Section)

The judgment section 118 judges whether or not the capsule 100 has reached a prescribed part, based on the picked-up images of inside the body cavity imaged by the imaging section 111. For example, the judgment section 118 judges whether or not the capsule 100 has reached the stomach, based on the picked-up images of inside the body cavity. The judgment section 118 outputs a judgment result to the control section 115.

Note that the judgment section 118 may judge whether or not the capsule 100 has reached the stomach based on values (pH values or the like) detected by various sensors (not shown in the figures) of the capsule 100.

(Control Section)

The control section 115 controls each constituent element of the capsule 100. Specifically, in the case where it is judged by the judgment section 118 that the capsule 100 has reached the stomach, based on the judgment result output from the judgment section 118, the control section 115 controls the stop section 119 so as to stop at the stomach.

Further, the control section 115, upon performing controls so as to remain at the stomach by the stop section 119, controls the stimulus generation section 117, and stimulates the stomach so as to provide a stimulus for promoting the burning of fat in the satiety center.

(Stop Section)

The stop section 119 has a function to make the capsule 100 remain inside the body cavity. There are various implementation methods of a stop operation by the stop section 119, and may be, for example, an arm type such as disclosed in JP 2005-204806A. An arm type is a stop operation in which the capsule 100 remains inside the body cavity by holding the mucous membrane on the body cavity inner wall with a plurality of arms.

(Stimulus Generation Section)

The stimulus generation section 117 provides a stimulus to the stomach, in accordance with the controls of the control section 115. Here, normally a person feeling a sense of fullness during a meal can be considered to be from a stimulus of the expansion of the stomach lining being transmitted from the brain. When the stomach lining is expanded by food filling the stomach, the vagus nerve (parasympathetic nerve) distributed in the stomach is stimulated, this is transmitted to the brain, and the satiety center is stimulated.

Therefore, the stimulus generation section 117 according the present embodiment generates a stimulus by expanding the stomach lining, and provides a stimulus to the satiety center. Specifically, for example, a balloon which has an airtight function with free expansion/contraction is included so as to cover the outer surface of part of the capsule 100, and the stomach liming may be expanded by expanding the balloon with a pressurized gas stored inside the capsule 100. In this way, the vagus nerve (parasympathetic nerve) distributed in the stomach is stimulated, this is transmitted to the brain, and the satiety center is stimulated.

Heretofore, the fat burning system according to the second embodiment has been described. Note that the stimulus generated by the stimulus generation section 117 is not limited to the above described stimulus which expands the stomach lining, and may be, for example, a stimulus which activates the activity of the stomach (promotes the motor functions of the stomach). It is possible to provide a stimulus to the satiety center of the brain by the activity of the stomach being activated.

Specifically, the stimulus generation section 117 is implemented by a release section, which releases medicine to activate the activity of the stomach, provided in the capsule 100 from a release opening included in the capsule 100. Note that the medicine to activate the activity of the stomach may be, for example, parasympathetic nerve stimulus medicine (carpronium chloride). Parasympathetic nerve stimulus medicine (carpronium chloride) activates the activity of the stomach (promotes the motor functions of the stomach) by improving the blood flow of the stomach.

<3. Conclusion>

As described above, the fat burning system according to the embodiments of the present disclosure can promote fat burning by providing a stimulus to fats inside the body cavity, or to the satiety center.

More specifically, in the fat burning system according to the first embodiment, fat burning can be promoted by providing a stimulus for ranges which include prescribed fats inside the body cavity. For example, the capsule 1 according to the first embodiment activates brown fat cells by cooling ranges which include brown fat cells, which include characteristics to burn fat, and can promote fat burning.

Further, in the fat burning system according to the second embodiment, a sense of fullness can be felt by providing a stimulus to the satiety center. In this way, since the brain transmits signals to the sympathetic nerves so as to consume additional energy, fat burning can be promoted.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below:

(1) A stimulus generation apparatus including:
a stimulus generation section which provides a stimulus for promoting fat burning for fat or a satiety center inside a body cavity.

(2) The stimulus generation apparatus according to (1),
wherein the stimulus generation section generates at least a mechanical, electrical, magnetic, or chemical stimulus.

(3) The stimulus generation apparatus according to (1) or (2),
wherein the stimulus generation section provides the stimulus by vibration, pressure, electricity, magnetism, or temperature change.

(4) The stimulus generation apparatus according to any one of (1) to (3), further including:
an imaging section which images inside the body cavity; and
a fat specification section which specifies the fat or a surrounding of the fat inside the body cavity by analyzing a picked-up image imaged by the imaging section,
wherein the stimulus generation section continuously or intermittently provides the stimulus for the fat or the surrounding of the fat specified by the fat specification section.

(5) The stimulus generation apparatus according to (4),
wherein the fat specification section specifies a brown fat cell by analyzing a color of the picked-up image, and
wherein the stimulus generation section provides the stimulus for a range which includes the brown fat cell.

(6) The stimulus generation apparatus according to any one of (1) to (4),
wherein the fat is a visceral fat or a vascular fat.

(7) The stimulus generation apparatus according to any one of (1) to (3),
wherein the stimulus generation section is a balloon capable of expanding or contracting in a stomach so as to provide the stimulus for promoting the fat burning for the satiety center, and
wherein the stimulus generation apparatus further includes:
a stop section for remaining at a prescribed part inside the body cavity; and
a balloon control section which stops inside the stomach by the stop section, and controls a size of the balloon.

(8) The stimulus generation apparatus according to any one of (1) to (3),
wherein the stimulus generation section is a release section which releases medicine to activate activity of a stomach so as to provide the stimulus for promoting the fat burning for the satiety center, and
wherein the stimulus generation apparatus further includes:
a release control section which controls the release section so as to release the medicine in a case where it is judged that the stimulus generation apparatus has reached the stomach.

(9) The stimulus generation apparatus according to (8),
wherein the medicine includes carpronium chloride.

(10) The stimulus generation apparatus according to any one of (1) to (6),
wherein the stimulus generation apparatus has an insertion section to be inserted into a body from a skin incision part, and
wherein the stimulus generation section is provided in a terminal of the insertion section.

(11) The stimulus generation apparatus according to any one of (1) to (9),
wherein the stimulus generation apparatus is a capsule type introduced into the body cavity.

(12) The stimulus generation apparatus according to (11),
wherein the stimulus generation apparatus includes a judgment section which judges whether or not the stimulus generation apparatus has reached a prescribed part.

(13) The stimulus generation apparatus according to (12), further including:
an imaging section which images inside the body cavity,
wherein the judgment section judges whether or not the stimulus generation apparatus has reached the prescribed part based on a picked-up image imaged by the imaging section.

(14) The stimulus generation apparatus according to (12), further including:
a communication section which communicates with an external apparatus, wherein the communication section transmits a signal for position detection to the external apparatus, and receives a control signal from the external apparatus, and wherein the judgment section judges whether or not the stimulus generation apparatus has reached the prescribed part based on the control signal received by the communication section.

The present disclosure contains subject matter related to that disclosed in Japanese Priority Patent Application JP 2012-180314 filed in the Japan Patent Office on Aug. 16, 2012, the entire content of which is hereby incorporated by reference.

What is claimed is:

1. A stimulus generation apparatus, comprising:
    a stimulus generation section configured to provide a stimulus to fat inside a body cavity or a satiety center to burn fat;
    an imaging section configured to image inside the body cavity;
    a fat specification section configured to specify the fat to which the stimulus is provided or a surrounding of the fat to which the stimulus is provided inside the body cavity by analysis of a color of a picked-up image imaged by the imaging section; and
    a display screen configured to show a plurality of parts within a body and an icon, to register a position of the stimulus, that moves to a determined part of the plurality of parts based on a user input.

2. The stimulus generation apparatus according to claim 1, wherein the stimulus generation section is configured to generate at least a mechanical, electrical, magnetic, or chemical stimulus.

3. The stimulus generation apparatus according to claim 1, wherein the stimulus generation section is configured to provide the stimulus by vibration, pressure, electricity, magnetism, or temperature change.

4. The stimulus generation apparatus according to claim 1, wherein the stimulus generation section is configured to continuously or intermittently provide the stimulus.

5. The stimulus generation apparatus according to claim 4, wherein the fat specification section is configured to specify a brown fat cell by analysis of the color of the picked-up image, and
    wherein the stimulus generation section is configured to provide the stimulus for a range which includes the brown fat cell.

6. The stimulus generation apparatus according to claim 1, wherein the fat to which the stimulus is provided is a visceral fat or a vascular fat.

7. The stimulus generation apparatus according to claim 1, wherein the stimulus generation apparatus includes a control section, the control section configured to judge whether a capsule that includes stimulus generation section has reached a prescribed part.

8. The stimulus generation apparatus according to claim 7, wherein the control section is configured to judge whether the capsule has reached the prescribed part based on the picked-up image imaged by the imaging section.

9. The stimulus generation apparatus according to claim 7, further comprising:
    a communication section configured to communicate with an external apparatus,
    wherein the communication section is configured to transmit a signal for position detection to the external apparatus, and receive a control signal from the external apparatus, and
    wherein the control section is configured to judge whether the capsule has reached the prescribed part based on the control signal received by the communication section.

10. The stimulus generation apparatus according to claim 7, wherein the control section is configured to extract information that corresponds to the prescribed part from a registered information database, the registered information database is communicably connected to the stimulus generation apparatus.

* * * * *